(12) United States Patent
Drummy

(10) Patent No.: US 8,670,952 B2
(45) Date of Patent: Mar. 11, 2014

(54) NON-DESTRUCTIVE INSPECTION INSTRUMENT EMPLOYING MULTIPLE SENSOR TECHNOLOGIES IN AN INTEGRAL ENCLOSURE

(75) Inventor: Michael Drummy, North Reading, MA (US)

(73) Assignee: Olympus NDT Inc., Waltham, MA (US)

( * ) Notice: Subject to any disclaimer, the term of this patent is extended or adjusted under 35 U.S.C. 154(b) by 470 days.

(21) Appl. No.: 13/088,698

(22) Filed: Apr. 18, 2011

(65) Prior Publication Data
US 2012/0265491 A1 Oct. 18, 2012

(51) Int. Cl.
*G06F 9/00* (2006.01)
(52) U.S. Cl.
USPC .......................................... 702/123; 702/121
(58) Field of Classification Search
USPC .............. 702/35, 38, 39, 121–123, 183, 185; 324/73.1; 341/155; 370/241, 242
See application file for complete search history.

(56) References Cited

U.S. PATENT DOCUMENTS

| | | | | |
|---|---|---|---|---|
| 7,817,076 | B2 * | 10/2010 | Drummy et al. | 341/155 |
| 2007/0039390 | A1 * | 2/2007 | Duncan et al. | 73/606 |
| 2007/0220946 | A1 * | 9/2007 | Pecina et al. | 73/1.01 |

* cited by examiner

*Primary Examiner* — Manuel L Barbee
(74) *Attorney, Agent, or Firm* — Ostrolenk Faber LLP

(57) ABSTRACT

A non-destructive inspection (NDI) instrument includes a sensor connection system configured to receive test signals from at least two different types of NDI sensors which are configured to obtain test signals from an object being tested. The sensor connection system has sensor-specific connection circuits and at least one common sensor connection circuit. A data acquisition circuitry is coupled to the sensor connection and has sensor-specific data acquisition circuits and at least one common data acquisition circuit. It is further coupled to a common digital data processor which executes sensor-specific processing modules and at least one common processing module. A common display screen and user interface is coupled to the data processor and enables programs including sensor-specific user interface modules and at least one common user interface module. The sensor types preferably include all of or any combination of an ultrasound sensor, an eddy current sensor and acoustic sensor.

40 Claims, 9 Drawing Sheets

NON-DESTRUCTIVE INSPECTION INSTRUMENT EMPLOYING MULTIPLE SENSOR TECHNOLOGIES IN AN INTEGRAL ENCLOSURE

BACKGROUND OF THE INVENTION

The present disclosure relates to non-destructive inspection (NDI) instruments, and more particularly to an instrument that is operable with multiple NDI sensor technologies, any one of which may be selected by the user.

Inspection service providers are among the largest users of NDI equipment. They have a broad customer base that requires many different inspection technologies to meet their inspection needs. For example, oil refineries require ultrasonic instruments to measure pipe and vessel wall conditions and detect flaws, aerospace companies require acoustic bond testing instruments to detect the composite material delamination, and eddy current instruments to detect cracks in metal surfaces of airplanes.

Ready access to these instruments by inspection service providers is of paramount importance because inspection events are often time critical and the type of inspection technology required is not always known with much advance notice. Due to economic constraints, it is not often practical to have a sufficient inventory of NDI instrument types to ensure that all inspection needs are met at any given time.

Another problem posed by the need for multiple NDI technologies concerns travel to remote and difficult to access inspections sites whether they are on land or at sea. Presently, the inspector needs to bring an application specific unit for each NDI technology required.

Previous attempts to mitigate these problems have involved integral and modular instrument packaging approaches. An example of a modular approach is the present assignee's OmniScan-MX product. This product has provisions for interchangeable acquisition modules, each that operate with a different NDI sensor technology; however, a separate acquisition module is required for each technology. Any one of the acquisition modules can be connected to a single processing/user interface unit which is significantly larger and heavier than any one of the acquisition modules alone.

The foregoing benefits described in relation to module interchangeability are accomplished to a lesser degree with the present assignee's Sonic, Bond Master and Nortec products, which are ultrasonic, acoustic and eddy current NDI technologies respectively. The interchangeability is limited to the display module alone; therefore, only it can be shared among the three base units each of which contains a different NDI technology. The base unit is much heavier and larger than the common display module.

An example of a system that is operable with multiple types of sensor technologies is Boeing corporation's MAUS-V product. The product employs a motorized scanner; each scanner is designed hold up to four sensors with spring-load mounts that adjust to complex contours. Up to four channels of full waveform ultrasonic or impedance plane eddy current data are collected at preset intervals as small as 1 degree. This data is stored on the computer disk and is later recalled for further review. Boeing MAUS-V product provides the usage of multiple sensors; however it has the drawbacks of using a computer and different data processing tools for data acquired from different types of sensors. The lack of using a common data acquisition and common data processing element in an integral and handheld enclosure presents an array of problems for field operation, including the weight and size of the product, the need for a lap top computer and high power consumption. The Boeing product does not allow battery operation. Another drawback is its high manufacturing cost.

An example of an integrally packaged multi-technology instrument is the MIZ-21SR eddy current and acoustic bond testing instrument provided by Zetec Incorporated of Snoqualmie, Wash., USA. However, this Zetec product does not allow the usage of conventional ultrasonic technology (i.e. >500 kHz) and there is no evidence showing that it employs a common sensor circuit and a data acquisition analog front-end and shares a common data processing. As a result, it failed to achieve the benefits of a versatile, high resolution instrument that allows smooth switching among usage of multiple sensors including UT, EC, acoustic, etc.

A example of an NDI system that uses shared circuit elements to minimize cost and circuit board size while providing different operating functions is disclosed in the present assignee's U.S. patent application Ser. No. 12/192,369 (i.e. Drummy et al), the entire content of which is herein incorporated by reference. The primary drawback of Drummy's teachings is that they are limited to the use of a 'set' of analog to digital converters that can be selectively used for either a multiple sensor array probe or a single element probe. Accordingly, the problem of sharing only one analog to digital converter circuit element to be selectively used to operate with multiple types of sensor technologies is not solved.

Considering the background information above, a solution that provides a plurality of NDI technologies to service providers in a manner to minimize the number of instruments they are required to maintain would be of great economic and ergonomic value.

SUMMARY OF THE DISCLOSURE

It is the general object of the present disclosure to overcome the problems associated with background art by introducing an economical, small, and compact instrument that contains multiple NDI technologies in the same package, any one of which may be activated by the user depending on the type of inspection being performed.

It is further an object of the present disclosure to provide at least two of the following user selectable NDI sensor technologies in a single instrument unit:
 a) Eddy Current flaw detection or electromagnetic conductivity measurement;
 b) Acoustic bond testing for laminated structures;
 c) Ultrasonic flaw detection, and thickness and corrosion measurement; and
 d) Magneto-acoustic corrosion measurement.

It is further an object of the present disclosure to maintain the factory or service center calibration integrity when switching between one technology mode of operating and another.

It is further an object of the present disclosure to utilize common hardware, software and mechanical parts to the fullest extent practical to minimize material cost and space.

It is further an object of the present disclosure to provide a user interface suitable for the type of sensor technologies mentioned in the present disclosure.

It is further an object of the present disclosure to provide a common user interface keypad suitable for at least two respective types of sensor technologies.

It is further an object of the present disclosure to provide either an encoder knob controlled user interface or up/down/left/right arrow keys controlled user interface to achieve the substantially same control end.

It is further an object of the present disclosure to minimize the number of sensor connectors by combining them in such a way as to be shared by two or more sensor technology types.

It is further an object of the present disclosure to render graphical user interface information on a high resolution (i.e. >320×240 pixel resolution) color display including C-scan renderings. Alternately, a display with gray scale rendering capabilities may be used.

It is yet a further object of the present disclosure to provide a convenient manual or semi-automatic means of sensor recognition to allow the NDI instrument to configure itself to work properly with the type of sensor technology connected.

It is yet a further object of the present disclosure to provide greater than a 20 V peak to peak excitation voltage to the acoustic type of sensor.

These and other objects of the present disclosure can be realized with an NDI instrument, wherein the NDI instrument includes: hardware and software compatible with the aforementioned NDI sensor technologies; a means to preserve calibration integrity when one sensor type is switched to another; a user interface suitable for each sensor technology; a sensor connection means allowing the sharing among different sensor types; and a means to automatically detect the sensor type and configure the instrument to operate in a suitable manner.

Other features and advantages of the present invention will become apparent from the following description of the invention which refers to the accompanying drawings.

DETAILED DESCRIPTION

Figure 1:
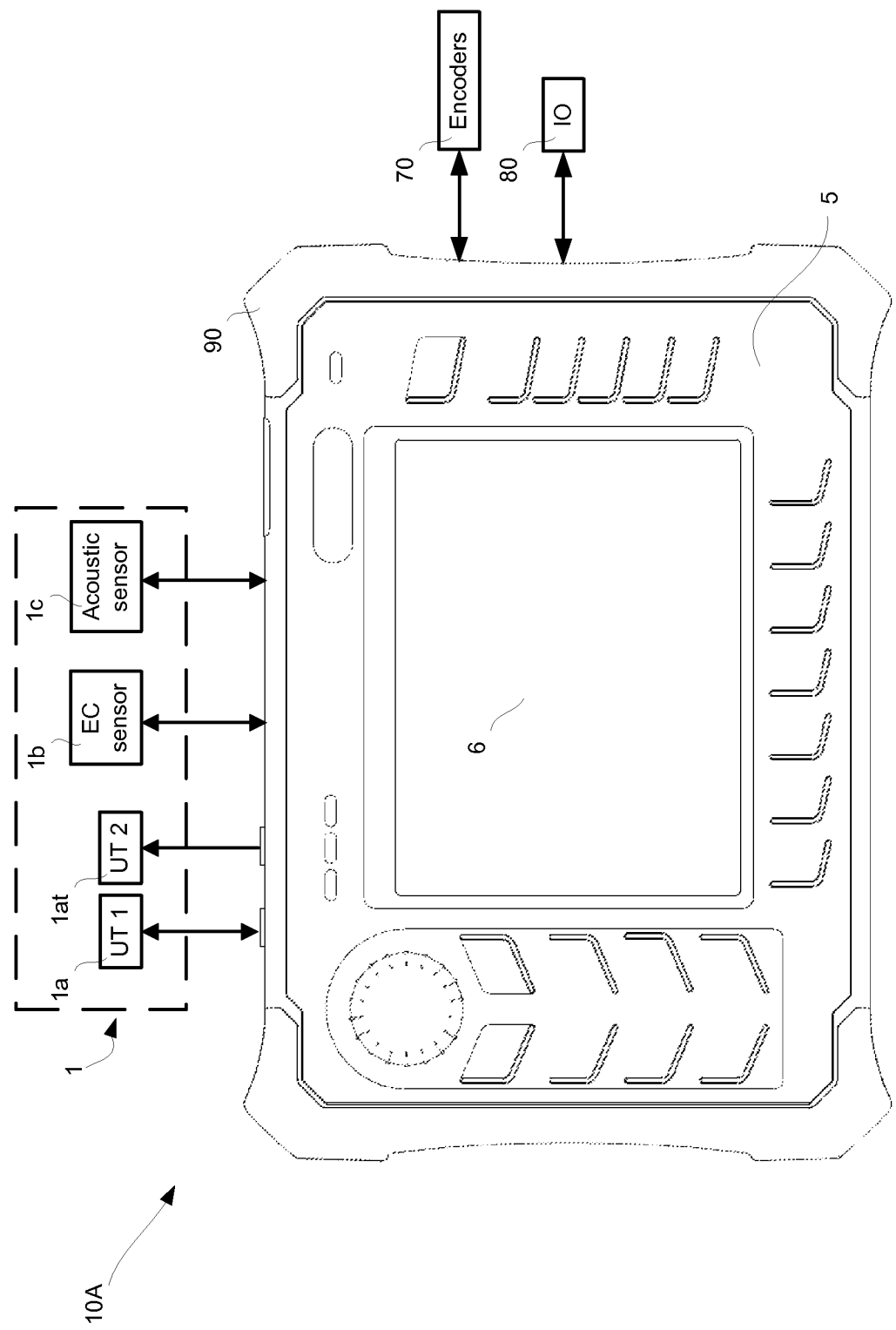
FIG. 1 is a exterior view of the portable integrated instrument according to the present disclosure.
Figure 2:
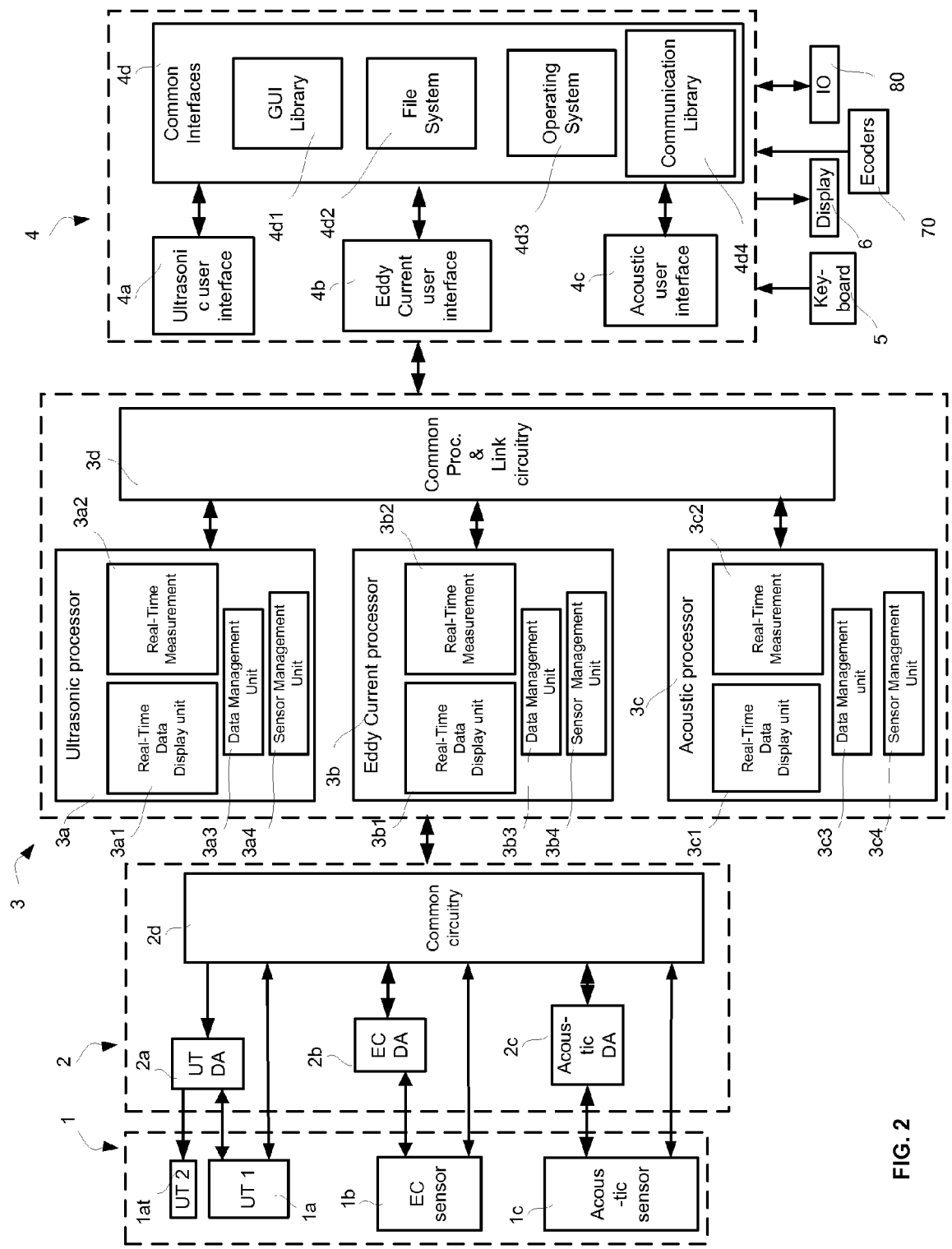
FIG. 2 is a schematic view of the system and sub-system components that comprise the preferred embodiment of the invention of the present disclosure.

FIGS. 1 and 2 depict an NDI device 10A enabling the usage of multiple sensor technologies according to the present inventio$_{[TL2]}$n. It should be noted that device 10A is also referred to as a 'system', wherein the 'system' as used is to describe the entirety of the preferred embodiment of the present disclosure, or an integrally packaged portable instrument as shown in FIG. 1; however, it is within the scope of the present disclosure for the term 'system' to apply to non-integral arrangements of hardware and software as well. For example, the sub-system elements described in the present disclosure need not be contained entirely in enclosure 90. They may be instead integrated into a sensor cable or other attachable device as required for the user's desired operating mode.

It should also be noted that the term 'sensor type' is intended to mean a type of sensor technology, such as ultrasound (UT), eddy current (EC), acoustic, hall effect, or magneto-strictive sensor technology. Furthermore, a given 'sensor type' may take the form of a single sensor or an array of sensors. It should also be noted that the term 'mode' as used in the present disclosure should be construed as an NDT instrument or device operating with one of the aforementioned sensor technologies.

The embodiments of the present disclosure are composed of an arrangement of 'common' (i.e. shared) and 'sensor type specific' (i.e. not shared) elements. The elements are comprised of the circuits, processes, and user interfaces that are required to operate an instrument with multiple sensor technologies. One of the primary objects of the present invention is to maximize 'common' elements and minimize 'sensor type specific' elements in order to achieve an optimal economy of size, weight, power and cost.

It should also be noted that subject titles herein used in the present disclosure only serves the purpose of presenting the content in an organized manner. The content under any subject title should be not construed with any limitation of the titles. For example, description under "Operating Mode" may disclose content related to apparatus structure, not only to operating procedures.

Referring to FIG. 1, from an exterior aspect, NDI device 10A is comprised of a sensor system 1, an enclosure 90, a keyboard 5, a display 6, encoders 70 and input/output port (IO) 80. Sensor int$_{[TL3]}$erface 1 is further comprised of at least one of the following 'types' of sensor technologies: Ultrasonic (UT) 1a, Eddy current (EC) 1b, or Acoustic 1c.

Figure 5:
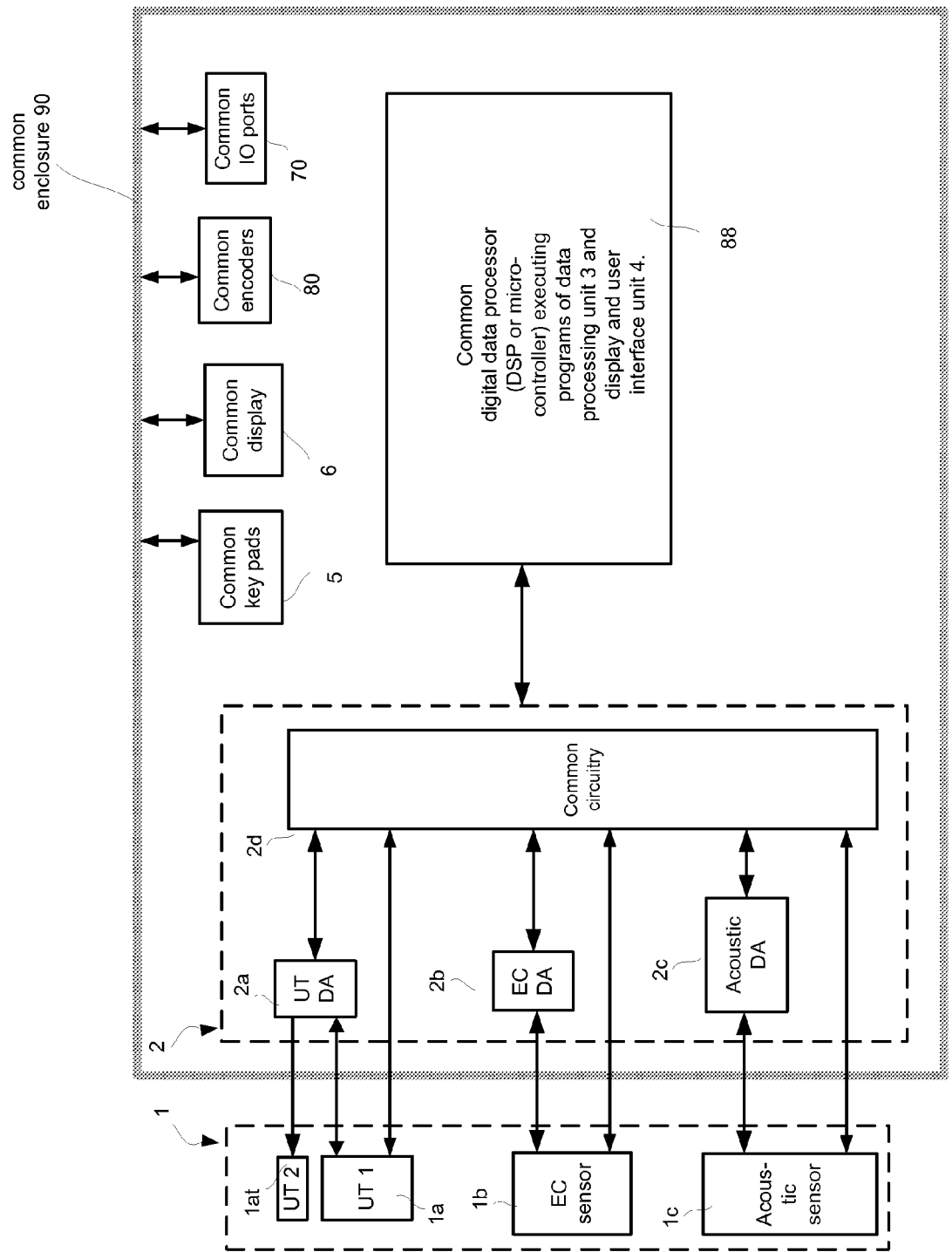
FIG. 5 is a schematic view of the system level of hardware components that comprise the embodiments of the present disclosure.

As shown in FIG. 2, NDI device 10A is further comprised of a data acquisition circuitry (DAS) 2, a data processing unit 3, and user interface unit 4, the later two of which are executable programs and are preferably loaded onto and executed by a common digital data processor 88 (FIG. 5). In an exemplary case shown in FIG. 2, all of the sensors in FIG. 1 are employed by NDI device 10A.

For notational convenience, a sub-system associated with a specific type of sensor technology is indicated by use of the letter a, b or c placed after the reference number. These letters are associated with sensor type UT 1a, EC 1b, or Acoustic 1c respectively. For example, the sub-system in data acquisition circuitry (DAS) 2 associated with an EC type of sensor 1b is 2b, for an acoustic type 1c it would be 2c, and so on. Accordingly, the respective association between sensor types, systems, and sub-systems is as follows: data acquisition unit (DAS) 2 comprises sensor-specific data acquisition circuits 2a, 2b, and 2c; processing unit 3 (executable programs) comprises sensor-specific processing modules 3a and 3a1~4, 3b and 3b1~4, and 3c and 3c1~4; and executable program user interface unit 4: 4a, 4b, and 4c.

Figure 3:
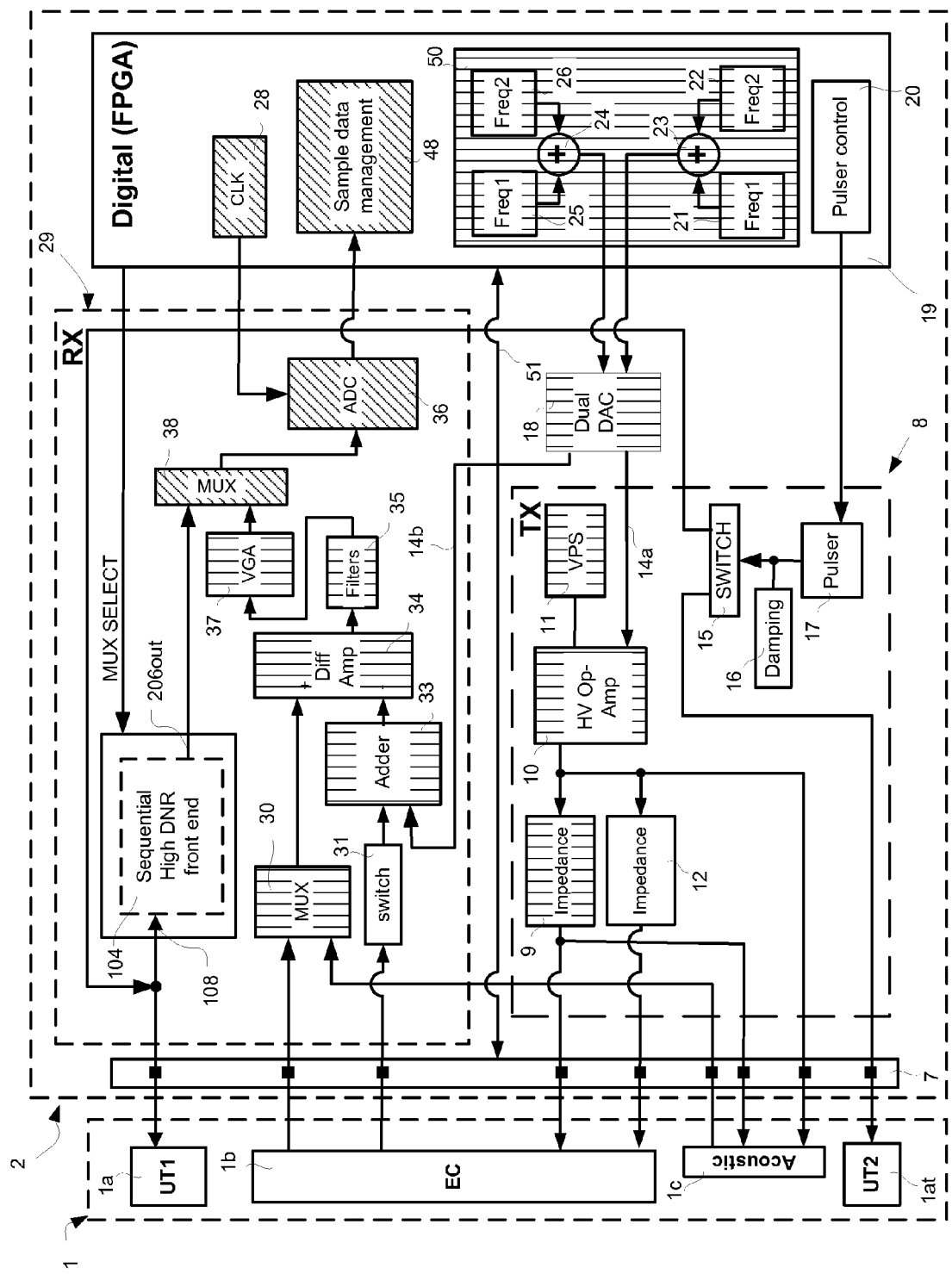
FIG. 3 is a schematic view of the system and sub-system components and software/firmware modules that comprise the preferred embodiment of the present disclosure.

UT sensor bat is the same type of sensor as UT sensor 1a; however, it is connected only to a pulser 17 preferably contained within data acquisition circuit 2a as shown in FIGS. 3, 4 and 5. UT sensor bat is intended for use in the 'pitch-catch' or 'through-transmission' NDI configurations that are well known to those skilled in the art.

Sub-systems that are common to at least two types of sensor technologies are sensor common circuitry 2d, common processing and link unit 3d, and interface unit 4d (3d and 4d are both executable programs.

Continuing with FIG. 2, an operating mode is now described in relation to exemplary sensor UT 1a; however, the description also applies to the other sensor types mentioned above unless otherwise stated. In other words, the ensuing description will be correct if the term 'UT sensor 1a' is replaced with 'EC sensor 1b' or 'Acoustic sensor 1c' along with their respective sub-systems. The composition and operation of system and sub-systems associated with each sensor type will be described in detail after the general overview below.

UT sensor 1a is coupled to UT data$_{[TL4]}$ acquisition circuit 2a and sensor common circuitry 2d. UT acquisition circuit 2a contains an excitation circuit to energize sensor 1a, and a receiver section that conditions the sensor response signal.

Common circuitry 2d contains an analog to digital converter to digitize the signals received from UT sensor 1a, another section of the receiver, and a data transfer and control interface that is coupled to an executable program, data processing unit 3 wherein UT processing module 3a is contained.

UT processing module 3a, an executable program, is comprised of a real-time data display module 3a1, a real-time measurement module 3a2, a data management module 3a3, and a sensor management module 3a4.

Continuing with FIG. 2, real-time data display module 3a1 is configured to construct a data representation based on the sensor response signal provided by circuitry 2d and the input parameters provided by means of keyboard 5. A succession of data representations is provided to user interface unit 4 to render the desired real-time measurement information on a display 6. Real-time measurement module 3a2 controls UT data acquisition circuit 2a and common circuitry 2d to provide real-time measurement activities and resulting data to UT processing module 3a. Data management module 3a3 stores and retrieves measurement data and user settings associated with measurement sessions. Default measurement setups and the identity of the sensor may be stored and retrieved as well. In some cases, a measurement setup will be associated with a sensor identity in order to automatically set up system operation. Lastly, sensor management 3a4 provides a means to query the sensor to determine its presence and identity, and to provide coefficients required to compensate the sensor to maintain a desired transfer function (e.g. calibration values).

Processing and link module 3d, an executable program, provides processes that are common to at least two of the sensor modes. The processes include: i) managing the interface between processing module 3 and user interface unit 4, ii) configuration and setup of UT processing module 3a, and iii) obtaining data from UT processing module 3a.

User interface unit 4, an executable program, includes UT user interface module 4a and common interface 4d which include a GUI library 4d1, a file system 4d2, an operating system 4d3, and communication library 4d4. These components in interface 4 can be discrete modules or in a form of any combinations.

Still referring to FIG. 2, UT user interface module 4a processes UT measurement data provided by common processing & link module 3d and the specific elements of the user interface associated with the use case for UT sensor 1a. These elements include a decoder decoding input from keyboard 5 and/or IO 80, graphical fields for display 6, and settings for encoders 70. GUI library 4d1 contains the display graphic primitives and framework associated with the UT sensor 1a which are invoked by operating system 4d3 as required. File system 4d2 provides a memory for the storage and retrieval of user configuration setup and measurement data. Operating system 4d3 performs the functions of a conventional real-time operating system that are well known to those skilled in the art. Operating system 4d3 includes program memory and RAM (not shown) and controls system activities in conjunction with processing module 3. Optionally a communication library 4d4 includes communication device drivers, such as USB, and a program application layer.

Referring now to FIG. 3, a more detailed description of the sensor system 1 and the data acquisition circuitry (DAS) 2 depicted in FIG. 2 is provided. The circuit elements shown in DAS 2 of FIG. 3 operate with one or more of the sensor types found in sensor system 1 described above. For ease of identification in FIG. 3, the circuit elements in DAS 2 have a unique background pattern to indicate the following:

a) Diagonal striped lines denote that element is commonly used for all three sensor types—i.e. elements analog to digital converter (ADC) 36, multiplexer (MUX) 38, sample data management unit 48, and clock 28.

b) Vertical striped lines denote that element is used for only EC sensor 1b and acoustic sensor 1c—i.e. elements MUX 30, adder 33, diff Amp 34, and filters 35, impedance 9, high voltage amplifier 10, variable power supply (VPS) 11, one output of dual digital to analog converter (DDAC) 18, and frequency synthesizer 50.

c) White background denote that element is used for only one sensor type—i.e. damping 16, SWITCH 15, pulser 17, pulser control 20, switch 31.

The circuit elements shown in FIG. 3, are selectively engaged to enable the operating modes described below. It should be noted for the ensuing description that a sensor connector system 7 may be composed of separate physical connectors for each sensor connected or integral physical connectors that can accommodate the connection of two or more sensors. Furthermore, connections are also provided by connector system 7 for sensor identification signals provided by a sensor (not shown) which are provided to FPGA 19 by means of signal 51. Sensor identification information is provided by FPGA 19 to processing unit 3 and user interface unit 4 to make appropriate settings associated with the particular sensor identified. Sensor identification information may be comprised of the sensor type, model number, serial number, date of manufacture, number of hours operated, calibration data and any other data that may be of interest to the user that is associated with the sensor. Sensor identification information is preferably stored within a sensor in a digital memory device; however, other identification means may be embedded with the sensor, such as a measurable parameter value that is associated with a specific sensor. Examples of parameter values are voltage and resistance.

Sensor Operating Modes

It should be noted for the foregoing description that the methods and apparatus required to excite sensors and receive and process the respective response signal are well known to those skilled in the art. Accordingly, such detail is not provided in the present disclosure. It should also be noted that the switch and MUX connections referred to for a specific operating mode are maintained in a fixed state throughout the operating mode—i.e. there is no dynamic switching during an operating mode. Furthermore, it should be noted that UT sensor 1a, EC sensor 1b, or acoustic sensor 1c are connected to connector system 7 for the respective operating mode described below.

UT Sensor Operating Mode

Continuing with FIG. 3, sensor energizer (Tx) circuitry 8 includes UT specific circuit elements pulser 17 and damping 16, the output of which is provided to either UT1 1a or UT2 1at depending on the UT function selected by the user by means of SWITCH 15. Pulser 17 is controlled by pulser control 20 which is implemented in FPGA 19.

Sub-system receiver (Rx) 29 includes UT specific front-end circuit 104. Receiver 29 further includes shared MUX 38 and ADC 36 which are used by all three sensor types. Clock 28 in FPGA 19 may be adjusted to provide a range of clock signal frequencies to ADC 36, which for the UT sensor mode is preferably 100 MHz. The response signal from sensor 1*a* is provided to the input of sequential high dynamic range front-end circuit 104 at an input point 108, both of which are shown in FIG. 2. The output of ADC 36 is provided to sample data management$_{[TL5]}$ unit 48 in FPGA 19.

The detailed methods associated with the aforementioned sequential high dynamic range front end 104 and input point 108 are disclosed in the present applicant's pending U.S. patent application entitled SENQUENTIALLY FIRED HIGH DYNAMIC RANGE NDT/NDI INSPECTION DEVICE (USPTO application Ser. No. 12/629,565). The entire content of application Ser. No. 12/629,565 is herein incorporated by reference. It should be noted that ADC 208 and input point 108 shown in FIG. 2 of application Ser. No. 12/629,565 and the corresponding text are intended to apply respectively to input point 108 and ADC 36 shown in FIG. 3 of the present disclosure. $_{[TL6]}$In FIG. 1 of application Ser. No. 12/629,565, Digital Logic Device 105 may be implemented in sample data management unit 48 in FPGA 19 of FIG. 3 of the present disclosure. Digital Memory Device 116 of application Ser. No. 12/629,565 may be implemented in FPGA 19 or in another memory device (not shown) of the present disclosure. Transmitter 101 of application Ser. No. 12/629,565 may be implemented in the same manner as pulser 17 of FIG. 3 of the present disclosure.

EC Sensor Operating Mode

Besides UT specific element, sensor energizer (Tx) circuitry 8 further includes shared circuit elements, i.e., a variable power supply (VPS) 11, a high-voltage amplifier 10 and impedance 9. These elements are used for both the EC and acoustic operating mode, the only differences between modes being the output voltage setting of VPS 11 and the output frequency setting of output 14*a* that is provided to the input of high voltage amplifier 10. One excitation coil terminal is connected to the output of impedance 9 and the other is connected to the output of impedance 12, both of which are preferably 10 ohms. Output 14*a* of dual DAC 18 is driven by the signal provided by summing node 23 in frequency synthesizer 50. The selected frequency provided by output 14*a* will preferably be within the range from 50 Hz to 12 MHz.

Besides UT specific element, receiver (Rx) 29 further includes shared circuit elements MUX 30, switch 31$_{[TL7]}$, adder 33, differential amplifier 34, filters 35 and VGA 37, all of which are used for both the EC and acoustic operating mode. Receiver Rx 29 also includes MUX 38 and ADC 36, both of which are used for the EC, UT and acoustic operating mode. When in EC operating mode, switch 31 connects one terminal of the sense coil of EC sensor 1*b* to one of the inputs of adder 33, and the other terminal to an input of differential amplifier 34 via MUX 30. The other input to adder 33 is provided by output 14*b* of DDAC 18, which is driven by the signals provided by summing node 24 in frequency synthesizer 50. Output 14*b* is used to null the sensed energizing AC signal at the output of switch 31 in order to better detect the sensed signal of interest, such as a flaw. The output of adder 33 is provided to the other input to diff amp 34, the output of which is provided to the input of filters 35. The output of filters 35 is provided to the input of VGA 37, the output of which is provided to the input of ADC 36 by means of MUX 38. The sample rate of ADC 36 is preferably 50 MHz and is controlled by clock 28 in FPGA 19. The output of ADC 36 is provided to sample data management unit 48 in FPGA 19 for processing.

Acoustic Sensor Operating Mode

Sensor energizer (Tx) circuitry 8 includes no acoustic sensor-specific circuit elements. Preferably, it shares all of the circuit elements used to energize EC sensor 1*b* except for impedance 9. The primary difference between the EC and acoustic excitation operating modes is the amplitude (preferably >20 V peak to peak) and frequency of the excitation signal provided to acoustic sensor 1*c* and the ability to use resonant and pitch-catch sensor modes for acoustic operation. The pitch-catch excitation sensor terminal is connected to the output of high voltage amplifier 10 and the resonant mode sensor terminal is connected to the output of impedance 9 which is preferably 10 ohms. High voltage amplifier 10 is driven by output 14*a* of dual DAC 18 which is driven by the signal provided by summing node 23 in frequency synthesizer 50. The selected frequency provided by output 14*a* will preferably be within the range from 200 Hz to 2 MHz.

Receiver (Rx) circuitry 29 includes all of the same shared circuit elements that are described above for the EC Sensor Operating Mode. When in acoustic operating mode, switch 31 disconnects one of the sense signals from EC sensor 1*b* and connects one of the inputs of adder 33 to ground. In addition to this, output 14*b* of dual DAC 18 is set to zero volts to disable the null effect of adder 33. The sense signal from acoustic sensor 1*c* is provided to an input of differential amplifier 34 via MUX 30. The output of adder 33 is provided to the other input to differential amplifier 34, the output of which is provided to the input of filters 35. The output of filters 35 is provided to the input of VGA 37, the output of which is provided to the input of ADC 36 by means of MUX 38. The sample rate of ADC 36 is preferably 50 MHz and is controlled by clock 28 in FPGA 19. The output of ADC 36 is provided to sample data management unit 48 in FPGA 19 for processing.

Overall System

FPGA 19 may have dedicated logic with full design image as would be the case for an ASIC, or just the design image required for a specific operating mode selectively loaded from memory. FPGA 19 may also be replaced with a microprocessor system that works with a program instruction set in the manner of a conventional embedded SW system; however, the real time performance of such systems is comparatively lower.

It should also be noted that to simplify the design, ADC 36 may be run with a fixed sample clock frequency, such as 50 MHz, for all three sensor operating modes. A higher sampling frequency can be obtained, such as 100 MHz, by use of interpolating filters located, but not separately identified, in FPGA 19.

Reference is now made to FIG. 5. It should be noted that both data processing unit 3 and display and user interface unit 4, including sub-system programs such as data processing modules 3*a, b, c* and *d* and display and user interface modules 4*a, b, c* and *d* are all executable programs which are preferably loaded onto and executed by a common digital processor 88. Digital processor 88 can be a digital signal processing chip (DSP) or a micro-controller chip. Digital processor 88 can alternatively takes the form of several sub-processors which are shared executable modules in 3 and 4. Digital processor 88 can be manufactured on a PCB board shared with sensor circuitry 1 and data acquisition circuitry 2. Processor 88 inter-connects with enclosure elements such as keyboard 5, display screen 6, encoder 70 and IO 80.

Sensor Identification and Selection of Associated Operating Mode

Figure 6:
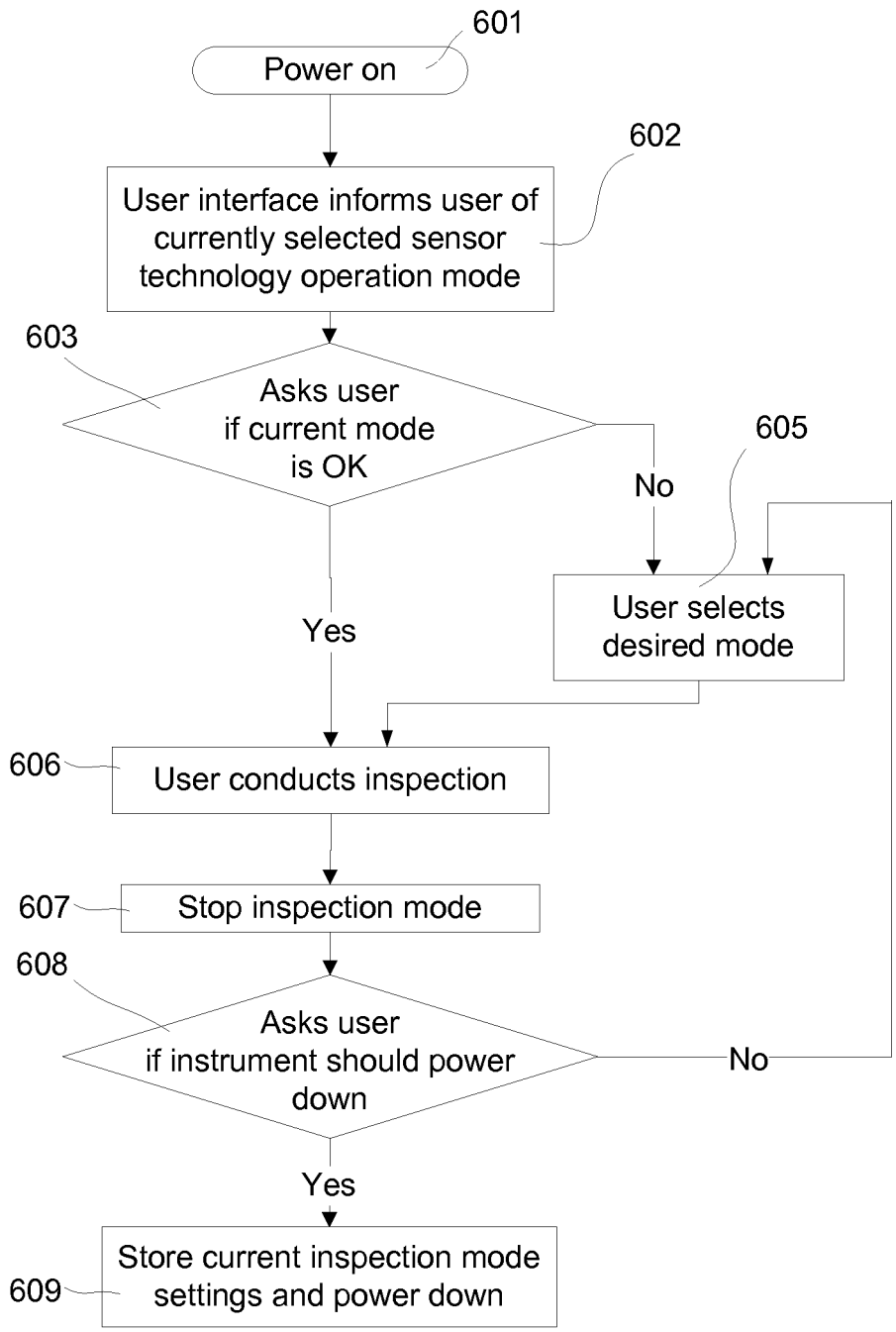
FIG. 6 is a flow chart view of the process of the present disclosure for manual sensor operating mode selection.
Figure 7:
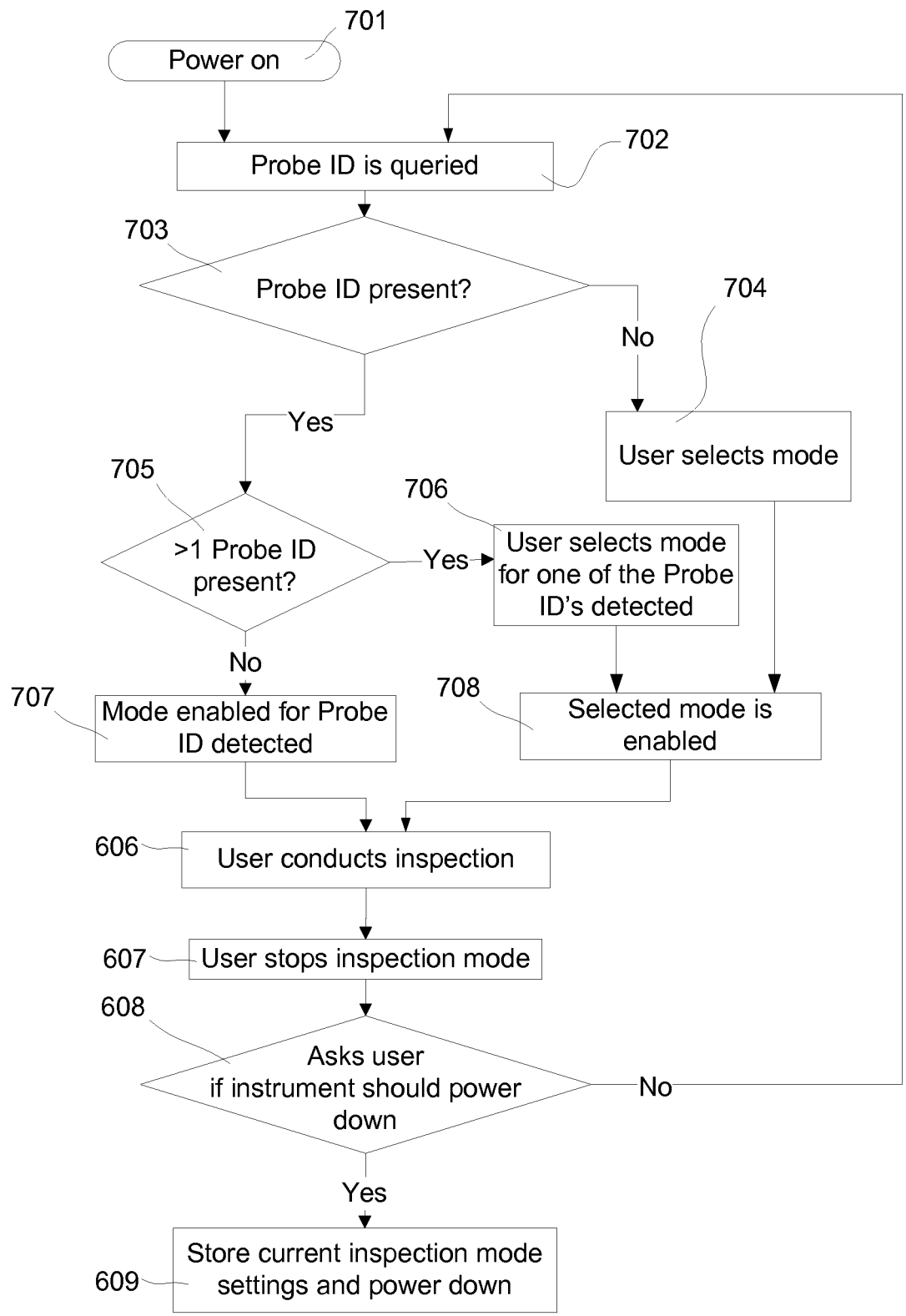
FIG. 7 is a flow chart view of the process of the present disclosure for semi-automatic sensor operating mode selection.

Referring now to FIGS. 6 and 7, an operating procedure and automatic method of sensor identification is described.

The flow chart of FIG. 6 applies to the manual sensor identification process wherein at step 601 the power is turned on, at step 602 the user interface informs the user of the currently selected sensor operation mode, and then at step 603 asks the user to indicate whether the current selected mode is acceptable. If the user answers 'yes', the inspection is performed by the user at step 606, the inspection session is stopped at step 607, and the user is asked by the user interface in step 608 whether the instrument should be power downed. If the user answers 'yes' at step 608, the current inspection mode settings are stored and the power is turned off at step 609. If the user answers 'no', he/she is asked to select the desired mode at step 605, after which steps 606 through 609 or 605 continue depending on the user's answer to step 608. If at step 603, the user answered 'no', then the user selects the desired mode in step 605 and the process continues from there as described above.

The flow chart of FIG. 7 applies to the automatic sensor identification process wherein at step 701 the power is turned on, at step 702 the instrument queries connector system 7 (FIGS. 3, 4 and 5) to determine the presence of sensors and the identification information contained therein. If it is determined at step 703 that a probe ID is not present, the user is prompted to select a sensor mode at step 704. This covers the scenario where a probe is used that has no sensor identification information, which will often be the case with existing commercially available sensors. The operating mode associated with the sensor mode selected at step 704 is enabled at step 708, after which the user conducts an inspection at step 606, and ends the inspection at step 607. Then, at step 608 the user is asked whether the instrument should be powered down. If the user answers 'yes' at step 608, the current inspection mode settings are stored and the power is turned off at step 609. If the user answers 'no', the process returns to step 702, and continues as described above. Table 1 is comprised of all of the elements shown in FIGS. 8*a* and 8*b* except for navigation keypad arrangement 89.

If at least one probe identity (ID) is present at step 703 and the number of ID's detected is determined to be greater than one at step 705, the user is asked to select which probe ID to use at step 706. Then the process proceeds to step 708 and continues from there as described above. If the number of ID's detected is determined to be one at step 705, the operating mode associated with the detected sensor is enabled at step 707. Then the process proceeds to step 606 and continues from there as described above.

Multi-Operating Mode Keyboard

Figure 8B:
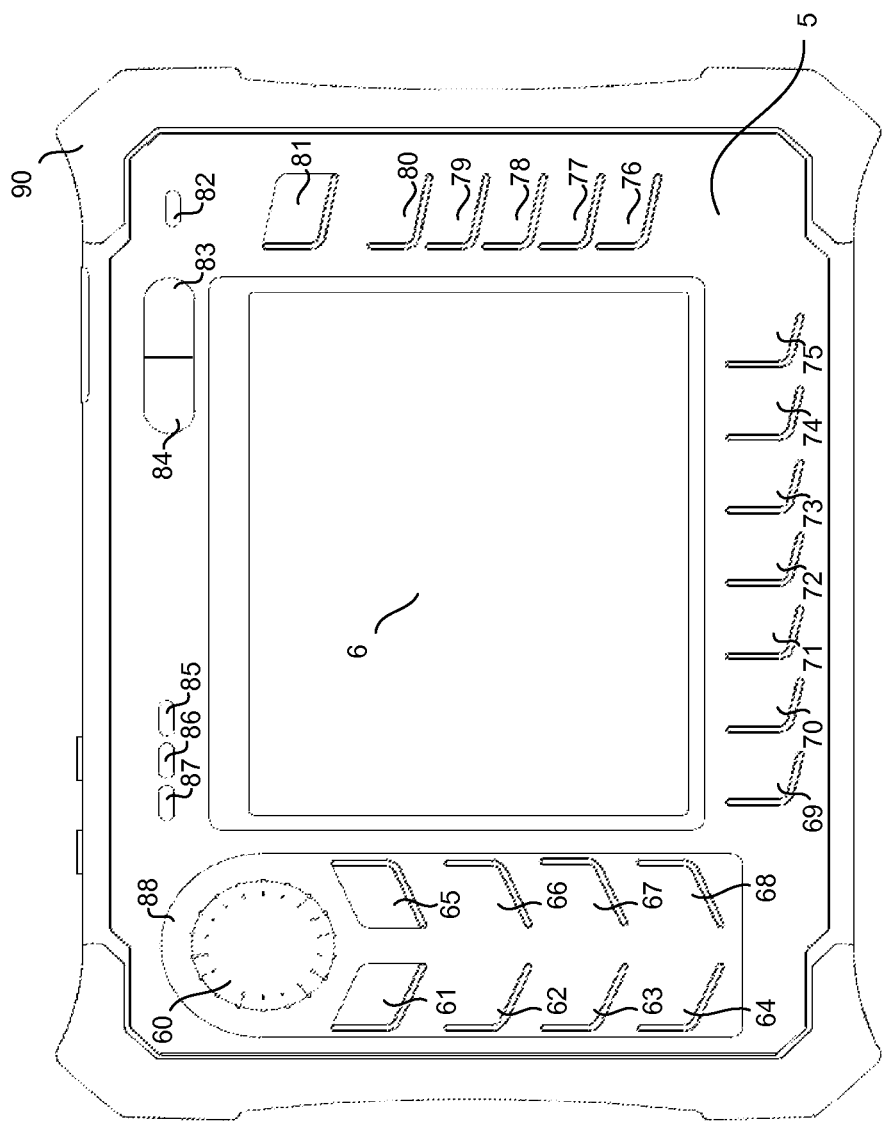
FIGS. 8a and 8b is a schematic view of the user interface of the portable integrated instrument of the present disclosure.
Figure 8A:
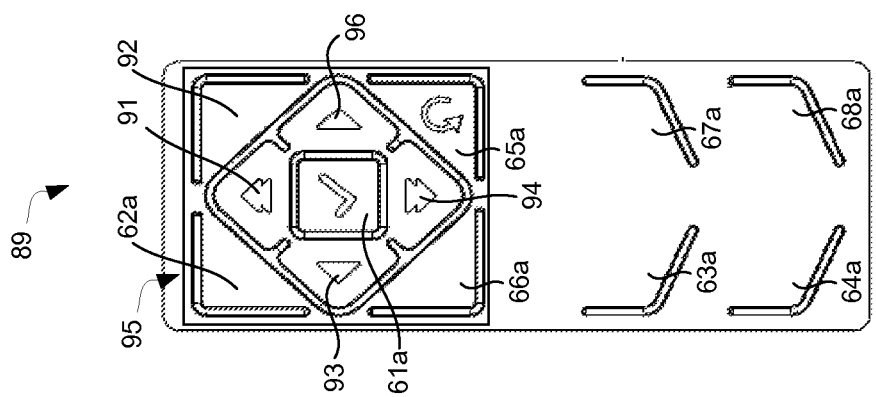

Referring to FIGS. 8*a* an$_{[TL8]}$d 8*b*, keyboard 5 can be used for any of the three sensor operating modes described in the present disclosure. The two embodiments of keyboard 5 are 'knob configuration 88' in FIG. 8*b* and 'navigation keypad configuration 95' in FIG. 8*a*, both of which are described in table-1 below. These embodiments allow the user to select an instrument with the type of user interface they prefer. 'Knob configuration 88' and 'navigation keypad configuration 95' provide the equivalent functions to the user. Accordingly, keys with equivalent functions share the same reference numerals in FIGS. 8*a* and 8*b*, except for a post-fix letter 'a' is placed at the end for configuration 88 in FIG. 8*a*.

The functional description of a key provided below for each keyboard element name in table-1 applies when the respective element is actuated by—e.g. actuating a key, illuminating a light, or turning a knob.

It should be noted that the term 'measurement image' as used in the present disclosure should be construed to mean either an impedance plane plot or time domain waveform of the sensor response along with associated numerical readings rendered on display 6. The term 'direct access key' should be construed to mean a key with direct access to software parameters that are commonly used during inspection Unless otherwise noted in the table below, the element function description applies to operating modes for UT sensor 1*a*, EC sensor 1*b* and acoustic sensor 1*c*.

TABLE 1

Adjustment knob 60:
Parameter values are adjusted by turning adjustment knob 60 when in a value selection mode. Preferably, values are increased by turning clockwise and decreased by turning counter-clockwise. A parameter type is selected by turning clockwise or counter-clockwise when in a parameter selection mode.
Check key 61 and 61a:
Is a general purpose key regardless of the instrument mode or function that has the following two primary functions:
1) When an adjustable parameter is highlighted, [the Check key] toggles the parameter adjustment between a coarse and a fine adjustment when adjustment knob 60 is used.
Coarse adjustment is indicated by brackets around the parameter key.
Fine adjustment does not have brackets.
2) Used to scroll through the menus in numerical order when navigation keypad 95 is used.
Null key 62 and 62a:
A direct access key that moves the dot on the impedance plane display or sweep display to a selected null position, which is typically located in the middle of the screen region where the measurement image is rendered.
This key is not used For the UT sensor 1a operating mode.
Erase key 63 and 63a:
A direct access key that erases the Screen measurement image and replaced it by next available measurement image.
This key is not used For the UT sensor 1a operating mode.
Freeze key 64 and 64a:
A direct access key that causes the current display image to remain unchanged.
ESCAPE key 65 and 65a:
A general purpose key regardless of the instrument state with three primary functions when actuated:
1) When in a setup page, returns to the live inspection screen. A setup page is a view used for user to select parameters or values for a particular operating function.
2) Whichever the selected menu, returns to the basic menu which is the top level screen image which cannot be accessed by any other means than by actuating the escape key.
3) When a direct access parameter is selected, will return to the previous menu.
Main key 66 and 66a:
A direct access key that accesses the MAIN menu that provides access to basic functions for instrument operation.
Alarm key 67 and 67a:
A direct access key that accesses the ALARM menu functions for alarm operation. This key is not used For the UT sensor 1a operating mode.
Setup key 68 and 68a:
A direct access key that accesses the SETUP menu to control various operating mode functions, such as: DATE and TIME settings, PROBE DRIVE, LANGUAGE settings, soft key left and right operation, and CAPTURE settings.
This key is not used for the UT sensor 1a operating mode.
Virtual parameter adjustment (VPA) keys 69 through 75:
The function of VPA keys is selectively assigned by user interface 4 of FIG. 1. These keys are used to adjust the function parameters invoked by actuating any of the VDA keys as described below.

TABLE 1-continued

Accordingly, a plurality of functions are assigned to any given VPA key, the instant name of which is rendered on display 6 in a region preferably above and in close proximity to the respective key.
Virtual direct access (VDA) keys 76 through 80:
The function of VDA keys is selectively assigned by interface 4 of FIG. 1. All VDA keys are grouped as whole sets, each set being associated with a particular functional context selected by the user. When a VDA key is actuated, the group of adjustable parameters assigned to it appears on display 6 in the VPA region for keys 69 through 75, as mentioned above. An exemplary assignment of VDA keys are described in Table-[TL9]2.
Save key 81:
Saves measurement information and/or settings to the selected or indexed File and ID. This key is not used for the UT sensor 1a operating mode.
Power/charge indicator 82:
Is preferably used as follows:
When the AC power is applied:
Green light indicates that the battery is fully charged.
Red light indicates that the battery is charging.
When the AC power is not applied:
Indicator light is off.
Power key 83:
Turns power on and off and provides a 'hard' reset when held pressed for an extended duration.
Lock keys key 84:
The user has the ability to lock knob 60 to prevent accidental parameter changes during an inspection.
Enunciator lights 85 through 87:
Visually indicates measurement alarm events or other aspects of the operating status.
Navigation keypad configuration 95 is comprised of the following keys:
Up key 91, Down key 94: these keys are used to increase and decrease a parameter value in coarse steps.
Right key 96, and Left key 93: these keys are used to increase and decrease a parameter value in fine steps.
Null key 62a: Same as described above.
$2^{nd}$ function key 92: Same as described in table 2 below.
ESCAPE key 65a: Same as described above.
Main key 66a: Same as described above.
Check key 61a: Same as described above.

The keys above that are not used for the UT sensor 1a operating mode are Null key 62 and 62a, Erase key 63 and 63a, Alarm key 67 and 67a, Setup key 68 and 68a, and Save key 81.

Continuing with FIG. 8b, for the UT sensor 1a operating mode, each of these physical virtual direct access keys 69~75 is exclusively assigned to a first and second function pair shown in table 2 below except for $2^{nd}$ function key 92.

TABLE 2

$2^{nd}$ function key 92:
Similar as to the convention of QWERTY keyboards used for computers, this key changes the function of the next, but different, key actuated compared to function it would have been if not preceded by the actuation of $2^{nd}$ function key. The $2^{nd}$ function is shown below enclosed in parentheses to the right of the first key function.
dB (REF dB) key:
dB: This direct access key enables the adjustment of system sensitivity (gain) in either coarse or fine increments.
REF dB: This direct access key establishes the current system gain as the reference (base) level which is useful for inspections that require the establishment of a reference gain level, and then the addition or subtraction of scanning gain.
GATES (AUTO xx %) key:
GATES: This direct access key enables the function that establishes at least one horizontal line segment on the waveform region of display 6 for the purpose of setting an amplitude threshold for the detection of at least one waveform event, such as the first passing edge, first peak, or maximum peak. These events may trigger alarms as well.

TABLE 2-continued

AUTO xx %: This direct access key automatically adjusts gated signal to XX % of full-screen height in the waveform region of display 6.
RANGE (DELAY) key: provides a means to manipulate the time base to focus on areas of interest on the waveform region of display 6.
RANGE: This direct access key sets the horizontal range of the waveform region of display 6 in inches or millimeters when the sound velocity is known for the material to be measured. Range may also be expressed in time, such as microseconds.
DELAY: This direct access key sets the horizontal location of the acquired waveform within the waveform region of display 6.
PEAK MEM (PEAK HOLD) key:
PEAK MEM: This direct access key function enables the display to capture and store on display 6 the amplitude of each A-scan acquisition. Display 6 updates each pixel if a signal of greater amplitude is acquired. When a sensor is scanned over a reflector, the signal envelope (echo dynamic as a function of sensor position) is held on display 6 as a distinctly colored line. In addition, the current, live waveform is displayed at the appropriate place within the signal envelope.
This function is useful when it is necessary to find the peak from an indication during an angle beam inspection.
PEAK HOLD:
This direct access key function is similar to peak memory as it captures the waveform region of display 6 when the function is accessed. The difference is that with peak hold, the captured waveform is frozen on display 6 and does not update even if the live waveform exceeds the frozen waveform's amplitude.
Peak hold is useful when you want to obtain a waveform from a known sample and compare it to a waveform from an unknown test piece. Similarities and/or differences in the waveforms can be noted to help determine the acceptance criteria for the unknown material.
FREEZE (SAVE) key:
FREEZE: This direct access key causes the current display image to remain unchanged.
SAVE: This direct access key saves measurement information and/or settings to the selected or indexed File and ID.

ALTERNATE EMBODIMENTS

Alternate Embodiment 1: Parallel High Dynamic Range Receiver for UT Sensor Mode

Figure 4A:
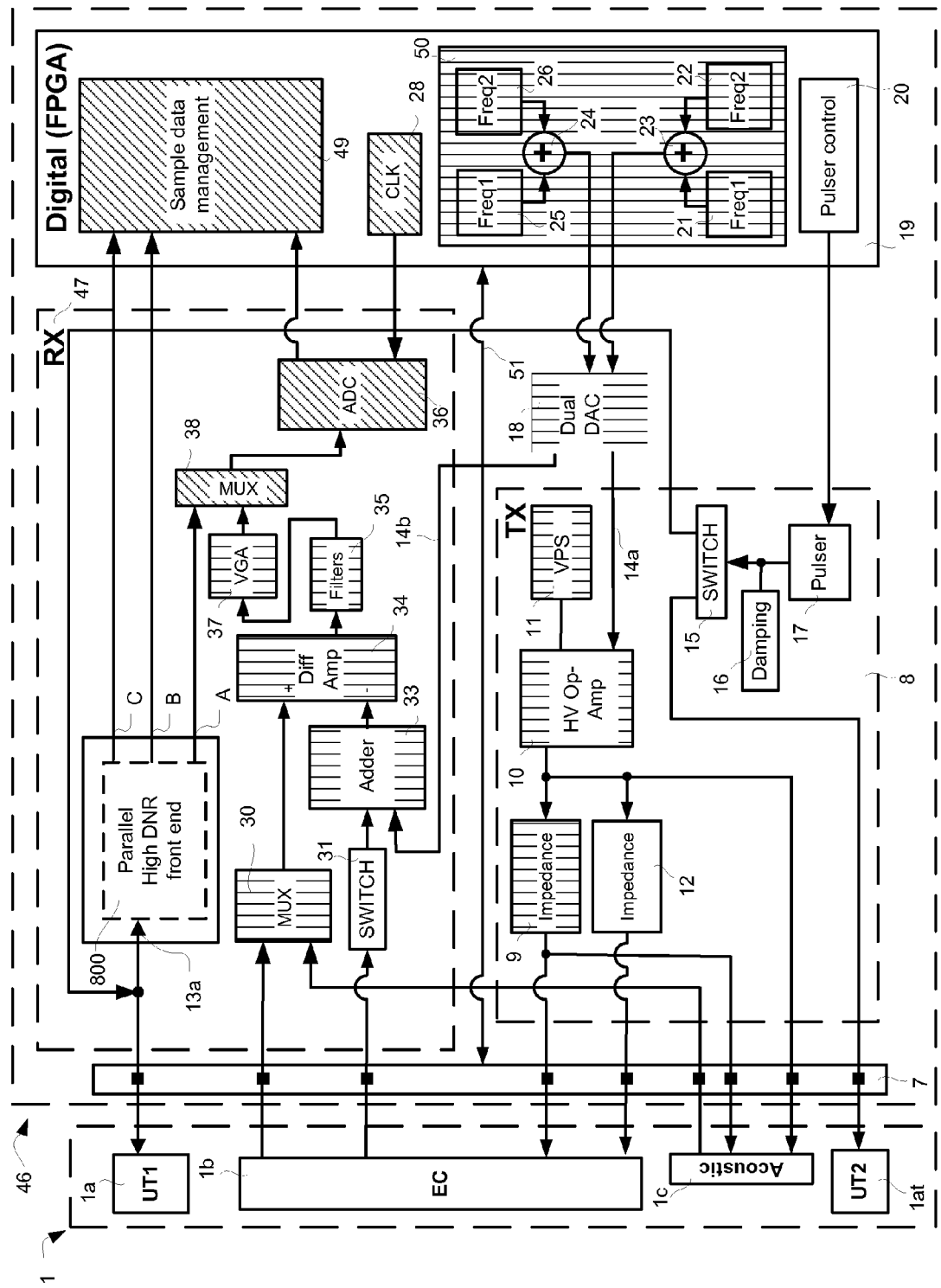
FIGS. 4a and 4b are schematic views of the system and sub-system components that is comprised by alternate embodiment 1 and the alternate embodiment 2 of the present disclosure.

Depicted in FIG. 4a, the subsequent description provides an embodiment with an alternative data acquisition circuitry 46, substituting data acquisition circuit 2 in FIG. 3. It should be noted that the entire description of the preferred embodiment shown in FIG. 3 applies to alternate embodiment 1 except for the description in the UT SENSOR OPERATING MODE section of the present disclosure that pertains to receiver sub-section 29.

Referring to FIG. 4a, receiver (Rx) circuitry 47 includes an alternate UT specific, parallel high dynamic range (PHDR) front-end circuit 800. Similar to the preferred embodiment, it also includes MUX 38 and ADC 36 that can be used by all three sensor types. Clock 28 in FPGA 19 may be adjusted to provide a range of clock signal frequencies to ADC 36, which for the UT sensor mode is preferably 100 MHz.

Detailed description of PHDR front-end circuit 800 is provided in U.S. patent application entitled ULTRASONIC FAULT DETECTION SYSTEM USING A HIGH DYNAMIC RANGE ANALOG TO DIGITAL CONVERSION SYSTEM with application Ser. No. 11/489,889, the entire content of which is herein incorporated by reference.

Particularly, in FIG. 4a of the present application, the response signal from sensor 1a is provided to the input of parallel high-dynamic range front-end circuit 800 at point 13a, both of which are shown in FIG. 8a of application Ser. No. 11/489,889 wherein transducer 12 is equivalent to UT sensor 1a of the present application. Output A of PHDR front end 800 in the present application is preferably provided to the input of ADC 36, the output of which is provided to sample data management 49 in FPGA 19. Outputs B and C of PHDR front-end 800 in the present application are respectively provided to differential drivers 128 and 130 shown in FIG. 8b of application Ser. No. 11/489,889. Furthermore, differential driver 126 of application Ser. No. 11/489,889 may be placed between the input of ADC 36 and the output of MUX 38 of the present application. ADC 36 of the present disclosure performs the same role as ADC 132 disclosed in application Ser. No. 11/489,889.

The detailed methods associated with the aforementioned PHDR front end circuit elements 800, input point 13a, outputs A, B and C, differential drivers of FIG. 8b application Ser. No. 11/489,889 126, 128 and 130, and ADC 132 are disclosed in application Ser. No. 11/489,889. Each of these reference numbers and letters has a direct correspondence between the present application and application Ser. No. 11/489,889.[TZ10]

Alternate Embodiment 2: Conventional Receiver for UT Sensor Mode

Figure 4B:
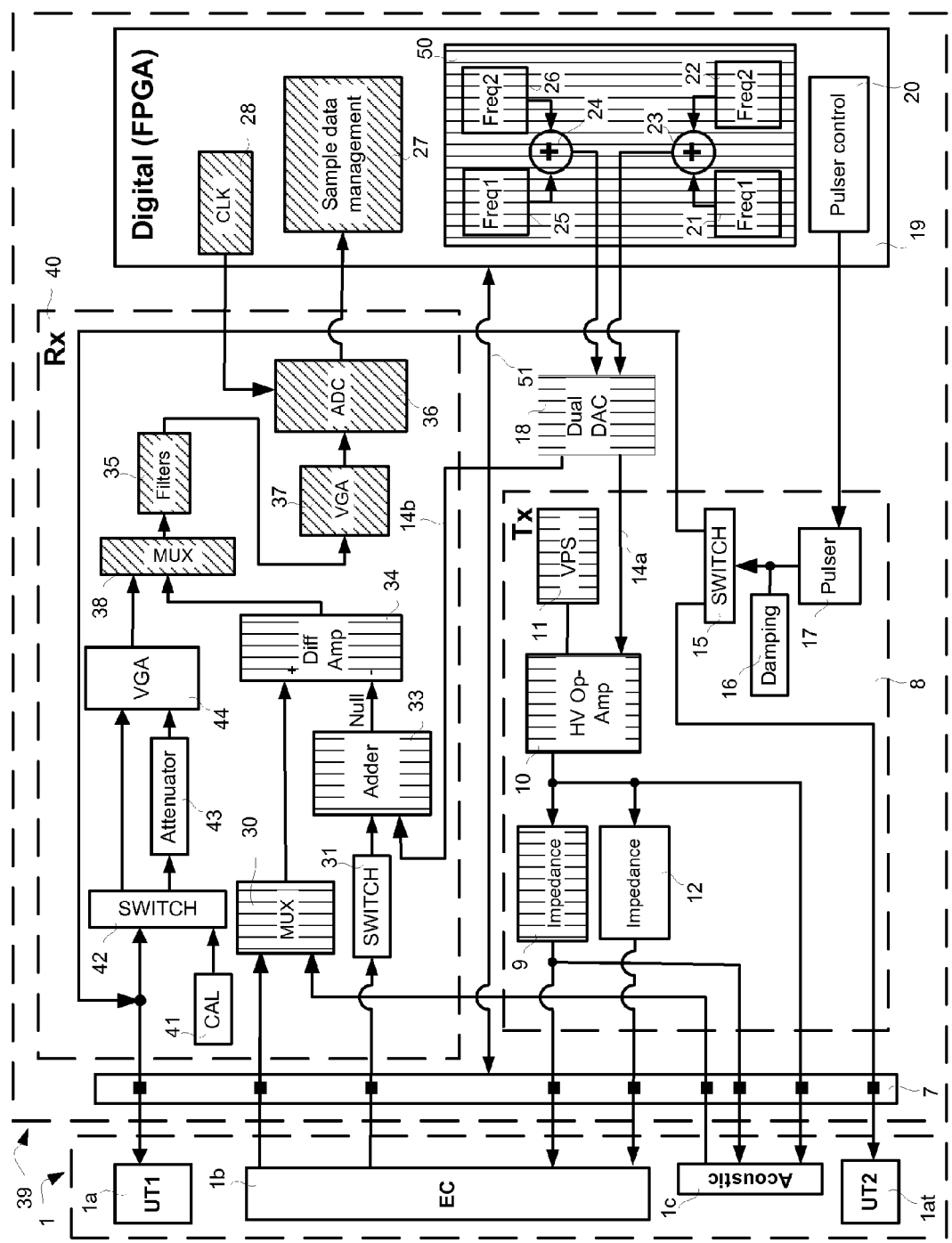

Alternate embodiment 2 of the present disclosure is now described in relation to FIG. 4b, in which another embodiment with an alternative data acquisition circuitry 39, substituting data acquisition circuit 2 in FIG. 3. More particularly, data acquisition circuitry 39 employs a front-end circuitry alternative to the sequential high-dynamic range circuit 104 in FIG. 3.

It should be noted that the entire description of the preferred embodiment shown in FIG. 3 applies to alternate embodiment 2 except for the description in the UT SENSOR OPERATING MODE section of the present disclosure that pertains to receiver circuitry 29 in FIG. 3.

Continuing with FIG. 4b, Receiver (Rx) circuit 40 includes UT specific circuit elements such as a calibration circuit (CAL) 41, a multi-pole switch 42, an attenuator 43, and VGA 44. MUX 38[TZ11], filters 35, VGA 37 and ADC 36 are used by all three sensor types. Clock 28 in FPGA 19 may be adjusted to provide a range of clock signal frequencies to ADC 36, which for the UT sensor mode is preferably 100 MHz. The response signal from sensor 1a and the output of calibration circuit 41 are provided to the input of switch 42; however, only one of them may be connected to an output of switch 42 at any given time. The gain of the two sensor signal paths within Rx sub-system 40 is calibrated by the signal provided by cal 41 which is selectively routed by means of multi-pole switch 42 to either VGA 44 or attenuator 43.

During an inspection session, sensor 1a is selectively connected to VGA 44 or attenuator 43 depending on the gain setting of the instrument. The output of VGA 44 is provided to the input of MUX 45, the output of which is provided to the input of filters 35. The output of filters 35 is provided to the input of VGA 37, the output of which is provided to the input of ADC 36. The output of ADC 36 is provided to the input of sample data management 27 located in FPGA 19. The processing methods for this data are well known to those skilled in the art.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A non-destructive inspection (NDI) instrument operable to conduct an NDI test on a test object, comprising:

a sensor connection circuitry configured to receive test signals from at least two types of NDI sensors, wherein at a given moment only one type of the NDI sensors is selected to obtain the test signals thereof from the object being tested, said sensor connection circuitry including at least two sensor-specific sensor circuits and at least one common sensor connection circuit;

a data acquisition circuitry processing said signals to digital data, including at least two sensor-specific data acquisition circuits and at least one common data acquisition circuit;

one or more digital data processors executing programs to process the digital data in a data processing unit and a display and user interface unit, wherein said data processing unit includes at least two sensor-specific processing modules and at least one common processing module, said display and user interface module including at least two sensor-specific user interface modules and at least one common user interface module, a display screen and a plurality of interfacing keys in communication with the display and interface module; and, a switching mechanism for selecting one sensor-specific sensor circuit from said sensor-specific sensor circuits, one sensor-specific data acquisition circuit from said sensor-specific data acquisition circuits, one sensor-specific processing module from said sensor-specific processing modules and one sensor-specific user interface module, and, for configuring said common sensor circuit, said common data acquisition circuit, said common processing module and said common interface module so that the instrument is operable to conduct the test suitable for said sensor circuit being selected.

2. The instrument of claim 1, wherein the at least two types of NDI sensors are of an ultrasound sensor, an eddy current sensor or an acoustic sensor.

3. The instrument of claim 2, wherein one or more of said NDI sensors has a single sensor configuration.

4. The instrument of claim 2, wherein one or more of said NDI sensors has an array sensor configuration.

5. The instrument of claim 2, including an excitation circuit to energize the ultrasound sensor and a receiver section configured to condition an ultrasound sensor response signal.

6. The instrument of claim 2, wherein the sensor-specific user interface modules include an ultrasound user interface module, an eddy current user interface module and an acoustic user interface module, all accessible and controllable via said display screen and interfacing keys.

7. The instrument of claim 2, wherein the sensor-specific data acquisition circuits include an ultrasound sensor-specific circuit which is configured to operate as a parallel high-dynamic range receiver for the ultrasound sensor.

8. The instrument of claim 2, wherein said sensor-specific data acquisition circuits include an ultrasound specific data acquisition circuit that is configured to include a switch coupled to the ultrasound sensor which has a calibration input, an attenuator and a VGA which has an output thereof which is coupled to an ADC that is driven from a clock which is comprised in said common data acquisition circuit.

9. The instrument of claim 2, wherein the sensor-specific data acquisition circuits include and ultrasound sensor-specific data acquisition in the formed as a sequential high dynamic range front end.

10. The instrument of claim 2, wherein the eddy current sensor and the acoustic sensor are configured to share one sensor-specific data acquisition circuit, which comprises at least an impedance, a high-voltage amplifier, a dual DAC, at least one frequency synthesizer, an adder and a differential amplifier.

11. The instrument of claim 1, wherein said NDI sensors are collectively configured to provide at least two of the following NDI sensor capabilities in single instrument unit including:
   a) Eddy Current flaw detection or electromagnetic conductivity measurement;
   b) Acoustic bond testing for laminated structures;
   c) Ultrasonic flaw detection, and thickness and corrosion measurement; and
   d) Magneto-acoustic corrosion measurement.

12. The instrument of claim 1, wherein said sensor connection circuitry includes at least one sensor connector which is configured to accommodate the connection of two or more of said at least two types NDI sensors.

13. The instrument of claim 1, wherein said display and user interface module and said interfacing keys are configured to enable users to select one type of NDT sensor from the at least two types NDT sensors and to switch from one type of NDT sensor to another.

14. The instrument of claim 1, further including sensor identification mechanism which identifies a particular type of sensor that is being connected to the instrument.

15. The instrument of 1, wherein said switching mechanism automatically conducts its function according to the type of sensor being selected.

16. The instrument of claim 1, wherein said instrument is configured such that it preserves calibration integrity when switching from one type of the NDT sensor to another.

17. The instrument of claim 1, said instrument being substantially a single-unit instrument, and wherein said data acquisition circuit and said digital data processors are housed in a single enclosure.

18. The instrument of claim 17, wherein said display screen and said plurality of interfacing keys are a part of said enclosure.

19. The instrument of claim 1, wherein said display and user interface module interfaces with said display screen and interfacing keys.

20. The instrument of claim 1, wherein said sensor-specific data acquisition circuits include a pulser, configured for use in a pitch-catch or in a through-transmission NDI configuration.

21. The instrument of claim 1, wherein the common data acquisition circuit includes a multiplexer, an analog to digital converter configured to digitize signals received from signals from any one of said sensor-specific sensor circuits and a sample data management module that is coupled to the processing unit.

22. The instrument of claim 1, wherein said common processing module is common to said at least two types of the NDI sensors and is configured to manage interfacing between said processing unit and said display and user interface module.

23. The instrument of claim 1, said common user interface module includes a GUI (Graphical User Interface) library, a file system, an operating system, and a communication library.

24. The instrument of claim 1, wherein said sensor-specific processing modules include a real-time data presentation module, a real-time measurement module, a data management module and a sensor management module for each type of the NDI sensors.

25. The instrument of claim 24, wherein the real-time data presentation module is configured to construct a data representation based on a specific sensor response signal received from the type of sensor being selected.

26. The instrument of claim 1, wherein said display and interface module produces screen shots onto said display screen and user interfacing keys can be in the form of keypads, keyboard, a set of virtual keys or key knobs.

27. The instrument of claim 26, wherein said set of keypads includes one of a knob configuration mode and a navigation keypad configuration mode.

28. The instrument of claim 26, wherein said keypads include at least a check key so that the resolution of the display screen can be toggled between higher resolution and lower resolution modes.

29. The instrument of claim 26, wherein said keypads include at least a direct-accessible null key, by which the user can move a dot on an impedance plane or sweep display to a selected null position on said display screen, which portion may be located in a middle of the display screen.

30. The instrument of claim 26, wherein said keypads include a direct access key, by actuation of which, said instrument erases a previous measurement screen shot and replaces it by a next available measurement screen shot.

31. The instrument of claim 26, wherein said keypads include a direct access key, by actuation of which, said instrument causes the present display screen shot to remain unchanged.

32. The instrument of claim 26, wherein said keypads include a direct access key, by actuation of which, said instrument returns the screen shot to a previous menu.

33. The instrument of claim 26, wherein said keypads include a direct access key, by actuation of which, said instrument returns and displays a main menu on the display screen.

34. The instrument of claim 26, wherein said keypads include a direct access key, by actuation of which, said instrument is prompted to provide alarms for measurement results deemed to trigger an alarm situation.

35. The instrument of claim 26, wherein said keypads include a direct access key, by actuation of which, said instrument enters into a setup mode that allow the user to set up measurement parameters such as date and time, probe drive and language settings.

36. The instrument of claim 26, wherein said keypads include a direct access key, by actuation of which, said instrument allows the user to set up the set of virtual keys.

37. The instrument of claim 36, wherein each of said set of virtual keys is designated differently for each corresponding sensor-specific sensor circuit.

38. The instrument of claim 36, wherein said set of virtual keys include a virtual key, by actuation of which, said instrument is prompted to save measurement information and/or settings to a selected or indexed file and sensor ID.

39. The instrument of claim 36, wherein said set of virtual keys or said keypads include a key, by actuation of which, said instrument is set up with a system gain as the reference level and a predetermined addition or subtraction of scanning gain.

40. The instrument of claim 36, wherein said set of virtual keys or said keypads include a key, by actuation of which, said instrument is set up with at least one horizontal line segment on a waveform region of said display screen for the purpose of setting an amplitude threshold for the detection of at least one waveform event including a first passing edge, a first peak, or a maximum peak.

* * * * *